(12) United States Patent
Sandmann et al.

(10) Patent No.: US 10,551,366 B2
(45) Date of Patent: Feb. 4, 2020

(54) SYSTEM AND METHOD FOR DRUG CLASSIFICATION USING MULTIPLE PHYSICAL PARAMETERS

(71) Applicant: Becton, Dickinson and Company, Franklin Lakes, NJ (US)

(72) Inventors: Christian Sandmann, Wayne, NJ (US); Erik Kurt Witt, Wyckoff, NJ (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 60 days.

(21) Appl. No.: 15/594,265

(22) Filed: May 12, 2017

(65) Prior Publication Data

US 2018/0328904 A1   Nov. 15, 2018

(51) Int. Cl.
*G01N 33/15* (2006.01)

(52) U.S. Cl.
CPC .................................. *G01N 33/15* (2013.01)

(58) Field of Classification Search
CPC ....................................................... G01N 33/15
USPC .......................................................... 702/25
See application file for complete search history.

(56) References Cited

U.S. PATENT DOCUMENTS

| | | | |
|---|---|---|---|
| 5,734,587 A * | 3/1998 | Backhaus | B01L 3/5085 382/133 |
| 6,512,936 B1 * | 1/2003 | Monfre | A61B 5/14532 128/920 |
| 8,728,025 B2 | 5/2014 | Bennett et al. | |
| 8,838,395 B2 | 9/2014 | Matsiev et al. | |
| 9,014,775 B2 | 4/2015 | Bennett et al. | |
| 9,052,276 B2 | 6/2015 | Matsiev et al. | |
| 2002/0043095 A1 * | 4/2002 | Mason | G01N 21/8483 73/1.02 |
| 2010/0305499 A1 | 12/2010 | Matsiev et al. | |
| 2012/0116687 A1 * | 5/2012 | Kanderian | C12Q 1/6827 702/20 |
| 2012/0143517 A1 * | 6/2012 | Abahri | G01N 33/28 702/25 |
| 2016/0363572 A1 * | 12/2016 | Blackley | G01N 33/15 |

* cited by examiner

*Primary Examiner* — Ricky Ngon
(74) *Attorney, Agent, or Firm* — Dickinson Wright PLLC

(57) ABSTRACT

A system and method for classifying a sample are provided. The system includes a housing containing the sample, a sensing element to measure at least one physical parameter of the same, and a processor configured to receive and analyze the physical parameter measurement, and to determine if the sample can be classified based on the measurement. If the sample cannot be classified, the processor selects and applies other analytical techniques until the sample is classified. The method includes selecting an analytical technique to apply to a sample, applying the technique to the sample, obtaining the results of the analytical technique, and determining if the sample can be classified based on the analytical technique. The method further includes selecting and applying further analytical techniques if the sample was not classified, until the sample is able to be classified.

8 Claims, 6 Drawing Sheets

SYSTEM AND METHOD FOR DRUG CLASSIFICATION USING MULTIPLE PHYSICAL PARAMETERS

FIELD OF THE INVENTION

The present invention relates to systems and methods for classifying drugs. In particular, the present invention relates to improved systems and methods for classification of drugs using multiple physical parameters.

BACKGROUND OF THE INVENTION

Medication errors remain a major problem in healthcare despite efforts to reduce mistakes. One approach to reduce drug errors is to positively identify drugs, diluent and concentration prior to administration. A number of chemical technologies can be employed to characterize drug solutions such as UV/Visual Spectroscopy, Raman Spectroscopy, Infra-Red Spectroscopy, Circular Dichroism, Refractive Index, Conductivity, pH and others. In fact, many of the traditional analytical tools have been used to identify drugs, but alone they would not be expected to identify a broad array of drugs and diluent solutions. Related information can be found in published PCT application number WO2009-114115A1 the contents of which are incorporated by reference herein in its entirety.

As one example, the chart in FIG. 1 illustrates the optical density spectra of Furosemide in normal saline (NS) diluent, Furosemide in D5W diluent, and D5W diluent alone. As illustrated, the optical density spectra of Furosemide in either diluent masks the spectrum of the diluent, preventing identification of the diluent by UV/Visual spectrum inspection alone.

One approach to improved identification of an IV compound was to use impedance spectroscopy. A small AC current was applied to the IV compound, and the AC current was swept in a range of frequencies to identify an impedance spectrum of the compound. However, this approach was not ideal because electrodes in contact with the interrogated fluid become fouled, and even when not fouled, impedance spectroscopy alone is not able to positively identify compounds and diluents satisfactorily.

Accordingly, there is a need for an improved system and method of identifying drug compounds and diluents.

SUMMARY OF THE INVENTION

The above described disadvantages are overcome and other advantages are realized by embodiments of the present invention, including a method for classifying at least one sample. The method comprises selecting an analytical technique to apply to the at least one sample, applying the analytical technique to the at least one sample, obtaining the results of the analytical technique applied to the at least one sample, and determining if the at least one sample can be classified based on the obtained results. If the at least one sample cannot be classified, the method further comprises selecting and applying another analytical technique.

Embodiments of the invention also provide a system for classifying at least one sample. The system comprises a housing for containing the at least one sample, at least one sensing element to measure at least one physical parameter of the at least one sample, and a processor configured to receive and analyze the at least one physical parameter, and determine if the at least one sample can be classified. If the at least one sample cannot be classified, the processor is configured to select and apply additional analytical techniques until the at least one sample is classified.

BRIEF DESCRIPTION OF THE DRAWINGS

Exemplary embodiments of the invention are described in connection with the appended drawings, in which.

Throughout the drawing figures, like reference numbers should be understood to refer to like elements, features and structures.

DETAILED DESCRIPTION OF EXEMPLARY EMBODIMENTS OF THE INVENTION

Exemplary embodiments of the present invention utilize multiple physical properties of medication solutions for classification of drug, diluent, and concentration. A combination of two or more physical measurements is used for drug characterizations including optical spectroscopy, fluid-mechanic, electrochemical, thermodynamic, and acoustic properties. Examples of optical spectroscopy measurements include, but are not limited to UV/Visual Spectrometry, Raman Spectroscopy, Infra-red spectroscopy, Circular Dichroic Spectroscopy, and Refractive Index. Examples of fluid-mechanic measurements include, but are not limited to mass density, specific weight, relative density, viscosity, surface tension, and Reynolds number. Examples of electrochemical measurements include, but are not limited to pH, electrical conductivity and conductivity spectra, impedance and impedance spectra, and admittance and admittance spectra. Examples of thermodynamic measurements include, but are not limited to heat capacity (specific heat) and thermal conductivity. Examples of acoustic measurements include, but are not limited to speed of sound, and time of flight. Many of these parameters are derived from other direct or indirect measurements of a fluid. Accordingly, it should be appreciated that the characteristics employed by exemplary embodiments of the invention are not limited to specific physical, chemical or mathematical definitions. Measurements are typically determined by measuring energy transmitted through the system, reflected back from the system, or energy used to interrogate a sensor that is within the fluid path.

It should also be noted that chemical and molecular probes may be employed to identify desired or contaminating constituents of an infusate. Antibodies, fluorescent dyes, bio-active molecules, DNA, nano-particles, electronic nose sensor, and so on, can be included in the fluid path where they are exposed to the fluid flow and volatiles and provide a signal that can be measured or transmitted to systems for analysis. These probes can be integrated into configurations where continuous exposure to fluids or volatiles is desirable, or could be exposed to the fluid for a limited amount of time, if using them to test the fluid disables them from being used again. For example, a drug binding with an antibody may not be reversible, so a sample and test, or one-time test approach would be a preferential test method.

These parameters can be used to verify the intended infusate, its concentration, as well as the presence of dissolved contaminates, wrong diluent, intermittent contamination, including particulates, infectious agents, and gasses (e.g., air bubbles).

Figure 1:
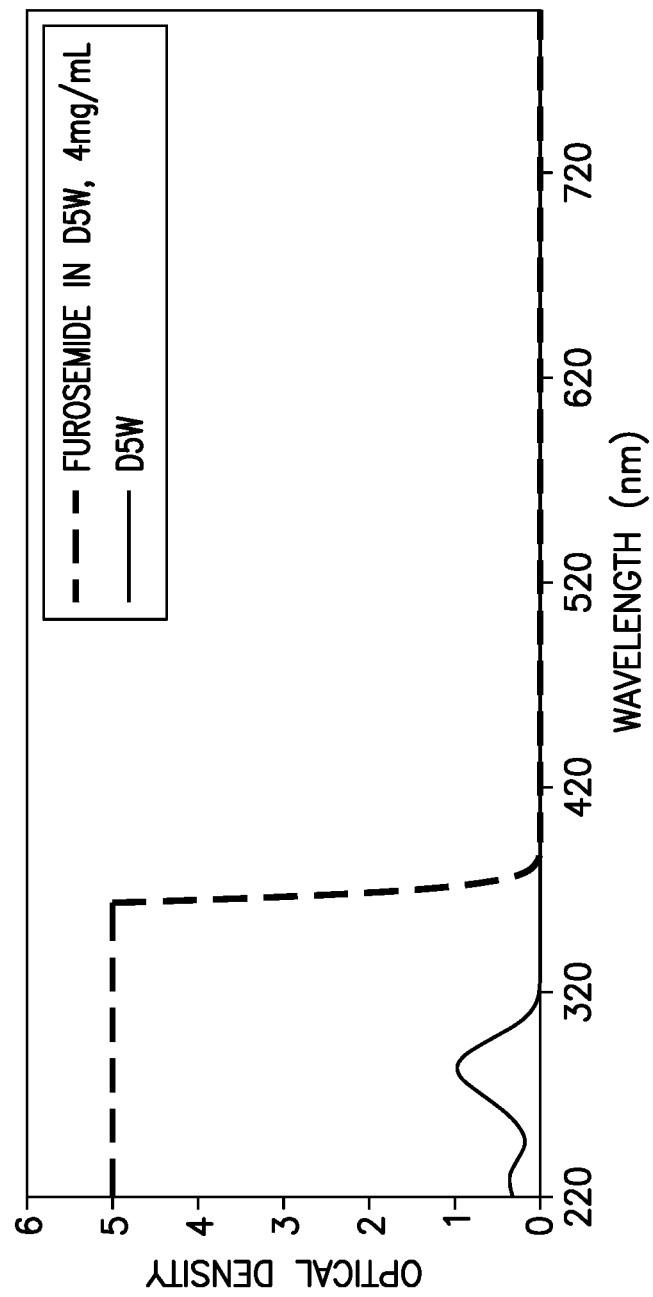
FIG. 1 illustrates the UV/Visual spectra of Furosemide in NS and D5W diluents, compared to the UV/Visual spectrum of D5W diluent alone.
Figure 2:
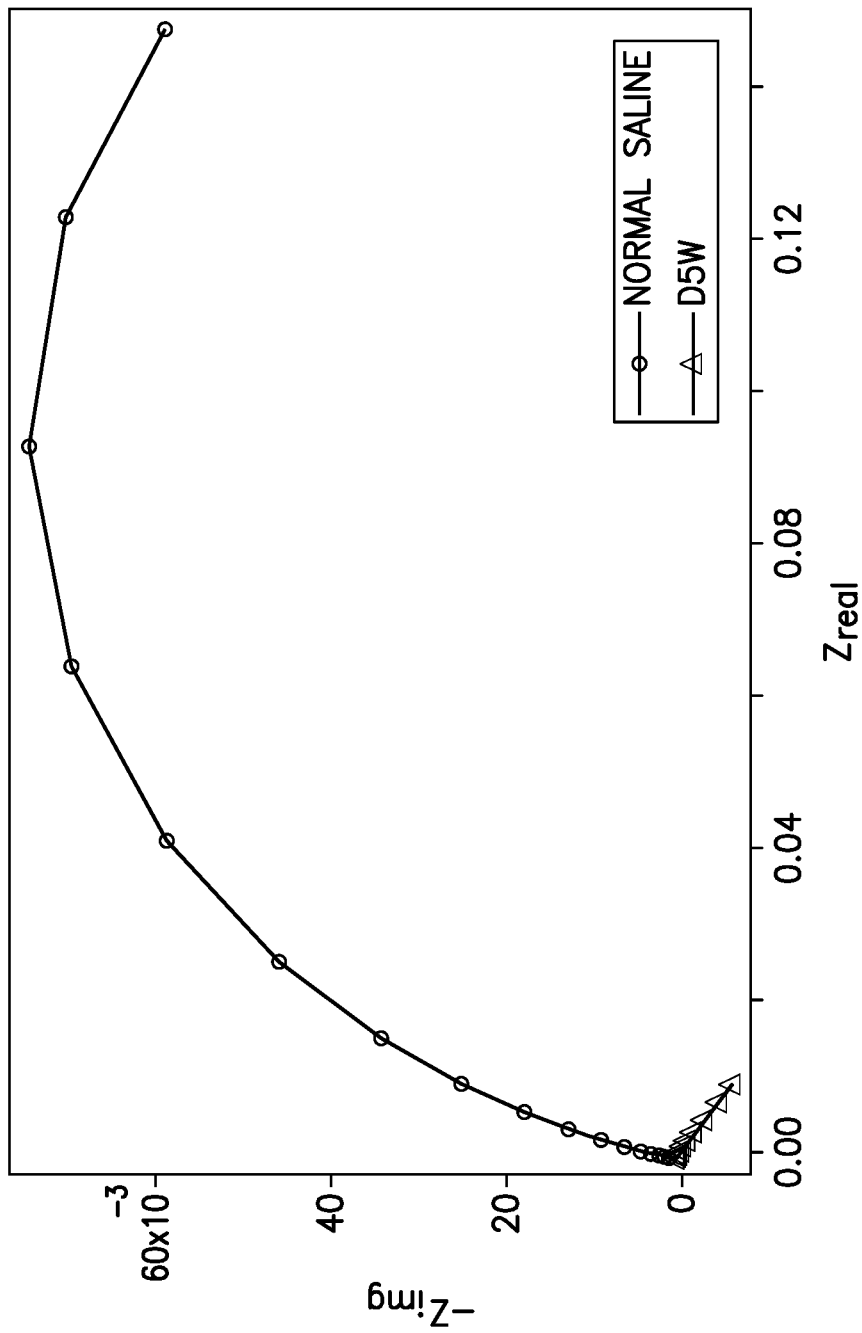
FIG. 2 illustrates impedance and admittance measurements of different diluents.

In some cases specific drugs and diluents can be identified with a single physical measurement to some extent, but in other cases drug solutions cannot be uniquely identified without combining measurements of multiple physical parameters. According to exemplary embodiments of the present invention, by advantageously combining measurements of different physical properties from multiple interrogation techniques, drug identification capabilities and accuracy are improved. For example, in some cases UV/Visual spectra alone can classify drugs to some extent, but the diluent is sometimes difficult to determine, such as for example when samples have a high absorption between 220-320 nm. FIG. 1 illustrates the UV/Visual spectrum measurements for Furosemide in NS diluent, Furosemide in D5W diluent, and D5W diluent alone. FIG. 1 also demonstrates the strong absorption of Furosemide in either NS or D5W, compared to the lower absorption of the diluent. Because the spectra of Furosemide in either diluent masks the spectra of D5W, UV/Visual spectroscopy alone is insufficient to positively identify the diluent. As illustrated in FIG. 2, however, the two diluents have different conductivity profiles. Accordingly, measuring impedance spectra and/or admittance spectra in addition to UV/Visual spectra increases determination accuracy. Refractive index may also be used in addition to or in lieu of the electrical properties described above. In one experiment using a support vector machine (SVM), conductivity was used to identify the diluent of a sample and based on this result either a drug library specific for D5W or normal saline was used to classify data measured with a UV/VIS spectrometer. Following this approach the drug identification performance for 10 drugs at 4 different concentrations in 2 different diluents improved from 70% correct drug identification to 84% moving from UV/VIS alone to a combination of conductivity and UV/VIS. In another experiment also using a support vector machine (SVM) classification method for 20 drugs at 4 different concentrations in 2 different diluents the overall accuracy to identify the diluent (D5W or normal saline) was 96%, which could further be increased to 100% by additionally using refractive index data. These experiments demonstrate that the combination of different analytical techniques improves the drug identification performance significantly.

In preferred embodiments of the invention, combinations of physical parameters are linked together to classify drugs before delivery to the patient. These assays could be performed on a single or multiple samples sequentially or simultaneously. An algorithm integrates the physical parameters for accurate solution identification. The algorithm classifies drug and diluent as well as concentrations by chemical properties and then interpolates between the calibration concentrations in a drug library.

Figure 3:
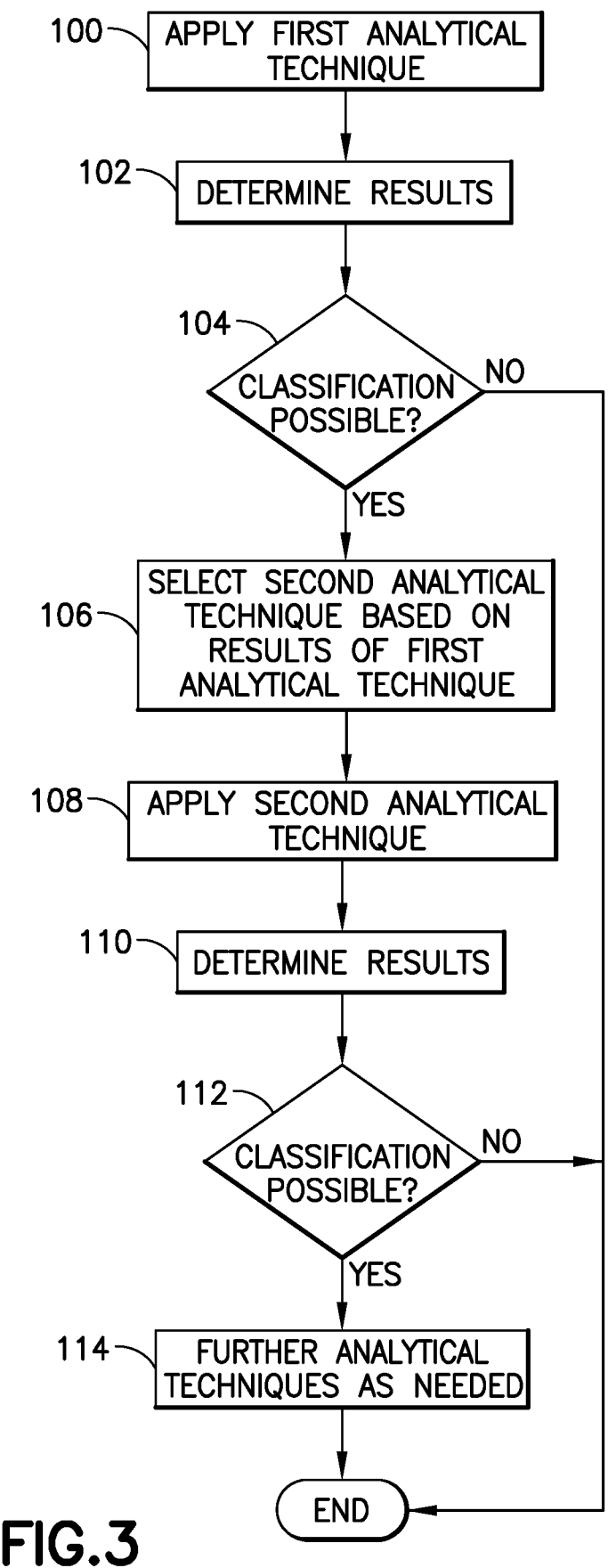
FIG. 3 illustrates a method according to an exemplary embodiment of the invention.

FIG. 3 illustrates an exemplary method according to an exemplary embodiment of the invention. At step 100, a first analytical technique is applied to an unknown sample. At step 102, the results of the first analytical technique are analyzed to determine if a unique drug and diluent may be classified, or if further properties must be measured. If a unique drug and diluent are classifiable based on the first analytical technique at step 104, then the drug and diluent are identified and the method ends. If, however, a unique drug and diluent were unable to be classified based on the first analytical technique, then the method continues to step 106, where a second analytical technique is selected to be applied to the sample. The second analytical technique is preferably selected based on the results of the first analytical technique to increase the likelihood of successfully classifying the drug and diluent. For example, as discussed above, if the first technique is UV/Visual Spectroscopy, the results may indicate Furosemide or D5W. Accordingly, the second technique to be selected would preferably be conductivity. At step 108 the second analytical technique is applied to the sample, and at step 110 the results of the second technique are determined. At step 112, if classification is possible based on the results of the second technique, then the method ends. If, however, at step 112 classification is still not possible, then further analytical techniques are selected and applied, as discussed above, and as generally shown as step 114. A classifier system that performs the above described exemplary method is preferably configured to include predetermined threshold parameters and features for a variety of drugs. A sample can be classified when the properties measured fall within predetermined threshold parameters.

While the classifier described above is stepwise, there are many classification algorithms known in the art of pattern recognition and machine learning that could be employed. If, during classifier training, it is determined that a subset of physical parameters are always required, then one or more of the classification steps could be multi-dimensional. Classification algorithms can be selected from parametric and non-parametric supervised methods such as discriminant analysis, decision trees, neural networks and support vector machines. Clustering, and regression (such as principle component analysis) algorithms, as well as many other methods known in the art can be employed.

In certain system architectures, it may not be necessary to completely characterize the infusate. The system can be designed to verify that no changes have occurred since the infusate left the pharmacy, where it was prepared. In this case, a certain set of physical parameters could be measured and recorded. Upon delivery to the patient site, prior to, or during injection, the same parameters could be measured. Allowing for measurement variability, and comparing the data from the two points in time, the confidence level that the drug is the same drug could be determined and reported to the clinician. An alarm or notification that an error has occurred would be indicated to the clinician. The system architecture can also be designed with a high fidelity system at the pharmacy where many infusate parameters are measured with high accuracy and precision. The system algorithm determines a subset of parameters, which will be measured with a lower fidelity system at the patient bedside to achieve the best possible confidence level that the drug has not changed.

In another embodiment, the system might be architected to detect if certain infusate characteristics can present safety hazards to the patient in an absolute sense, while other characteristics may be reported in a qualitative sense. For example, if the ionic content (salinity) is significantly higher than physiologic levels, there can be cardiovascular implications. Bulk electrical impedance can be utilized to measure ionic content, and used to report a hazard separately from other hazards. The same impedance data could then be used in combination with other measured fluid properties in a classifier to report on the likelihood of another medication error, such as the wrong drug for a particular patient.

Many of the embodiments described above require comparison of infusate property data from two or more locations and times. In addition, knowledge of the original patient prescription, the constituents of the infusate drawn from pharmacy or hospital inventory, the steps involved in reconstitution and preparation and the method of delivery to the patient may be required to enable the system. These data are available in information and workflow systems used in hospitals and hospital pharmacies today. Further, technologies used for wired and wireless transmission of data, and machine-readable coding and readers (e.g., RFID, barcode scanners) are widely known in the art. Infusate parameter generation, communication, processing algorithms, reporting, storage and alerting can be implemented with any number of architectures, on single or multiple processors, on local or remote networks, in one or more housings. There are of course tradeoffs between different architectures that are known to those skilled in the art and do not require detailed descriptions herein to fully implement, so they are omitted for efficiency and brevity.

A classifier system is preferably previously configured to include predetermined threshold parameters and features for a variety of drugs. A sample can be classified when the properties measured fall within the predetermined threshold parameters.

It should also be noted that chemical and molecular probes may be employed to identify desired or contaminating constituents of an infusate. Antibodies, fluorescent dyes, bio-active molecules, DNA, nano-particles, etc., can be included in the fluid path where they are exposed to the fluid flow and provide a signal that can be measured or transmitted to systems for analysis. These probes can be integrated into configurations where continuous exposure to fluids is desirable, or could be exposed to the fluid for a limited amount of time, if using them to test the fluid disables them from being used again. For example, a drug binding with an antibody may not be reversible, so a sample and test, or one-time test approach would be a preferential test method.

These parameters can be used to verify the intended infusate, its concentration, as well as the presence of dissolved contaminates, wrong diluent, intermittent contamination, including particulates, infectious agents, and gasses (e.g., air bubbles).

Embodiments of the present invention have advantages over prior art in that solution characterizations are more specific by using multiple physical properties rather than just one. For example, it is difficult to identify Furosemide diluent solutions by UV/Visual spectra alone as its specific signal overlaps with the diluent signal. Many high absorbing drugs have similar overlapping properties. If conductivity measures are employed with UV/Visual spectra, then both drug and diluent can be identified. In a similar fashion, two drugs might have comparable UV/Visual spectra and be difficult to classify, but may be distinguished by specific Raman Spectra or other analytical techniques.

An additional advantage of the invention is that single use probes could be conserved if adequate characterization of the infusate can be made without using or otherwise consuming them.

Figure 4A:
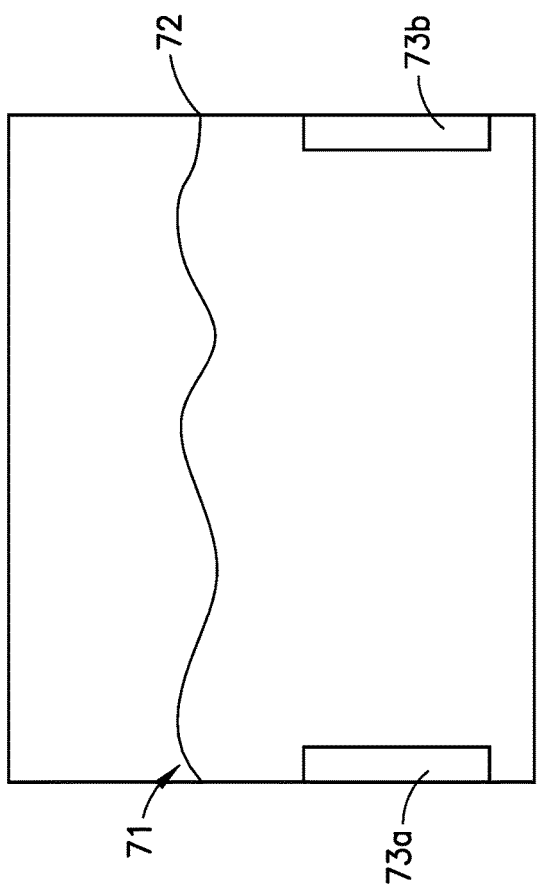
FIG. 4A illustrates a system for drug classification including a static drug sample interrogated in a container.
Figure 4B:
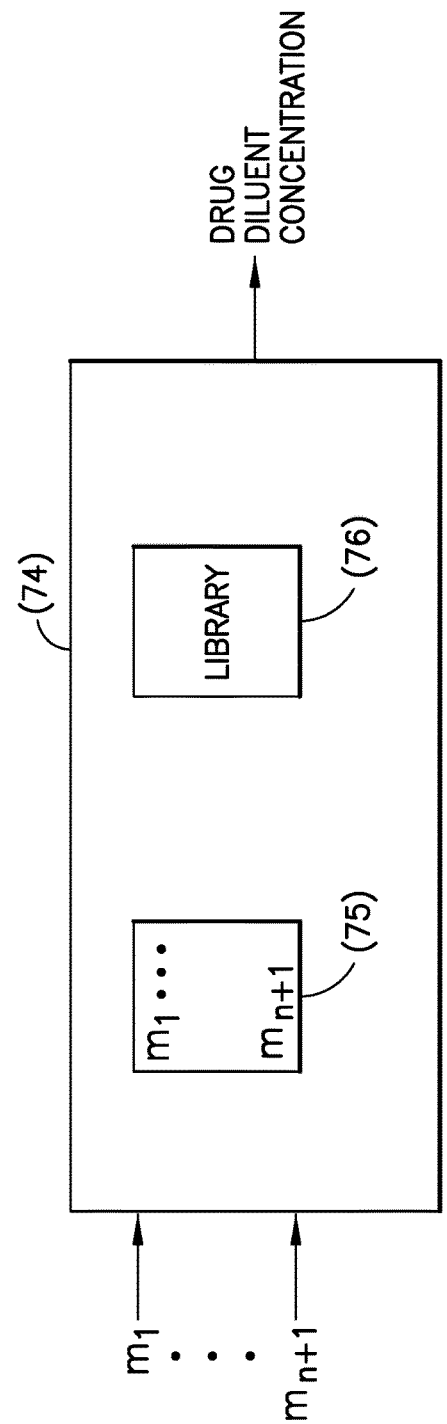
FIG. 4B illustrates an algorithm for classifying the drug in the system of FIG. 4A.

FIG. 4A illustrates an exemplary system according to the present invention. A static drug sample (71) is interrogated in a container (72) with one or more physical techniques such as those discussed above. For example, optically neutral containers could be assayed by UV/Visual, Raman Spectroscopy, or Refractive Index in one system to obtain measurements $M_1 \ldots Mn$. If conductivity needs to be measured, then electrodes (73a, 73b) can be added to the assay container (72) to obtain Mn+1. FIG. 4B illustrates a device 74 using an algorithm to compile the solution properties of unknowns ($M_1 \ldots Mn+1$) (75) and compare them to a library of known drugs (76). This embodiment is suitable for use in a compounding pharmacy to confirm accurate drug compounding prior to delivery.

Figure 5A:
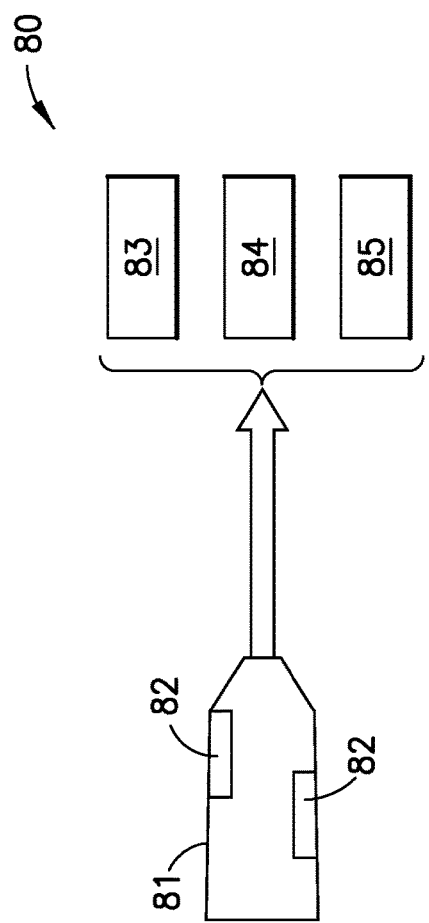
FIG. 5A illustrates a system for drug classification including.
Figure 5B:
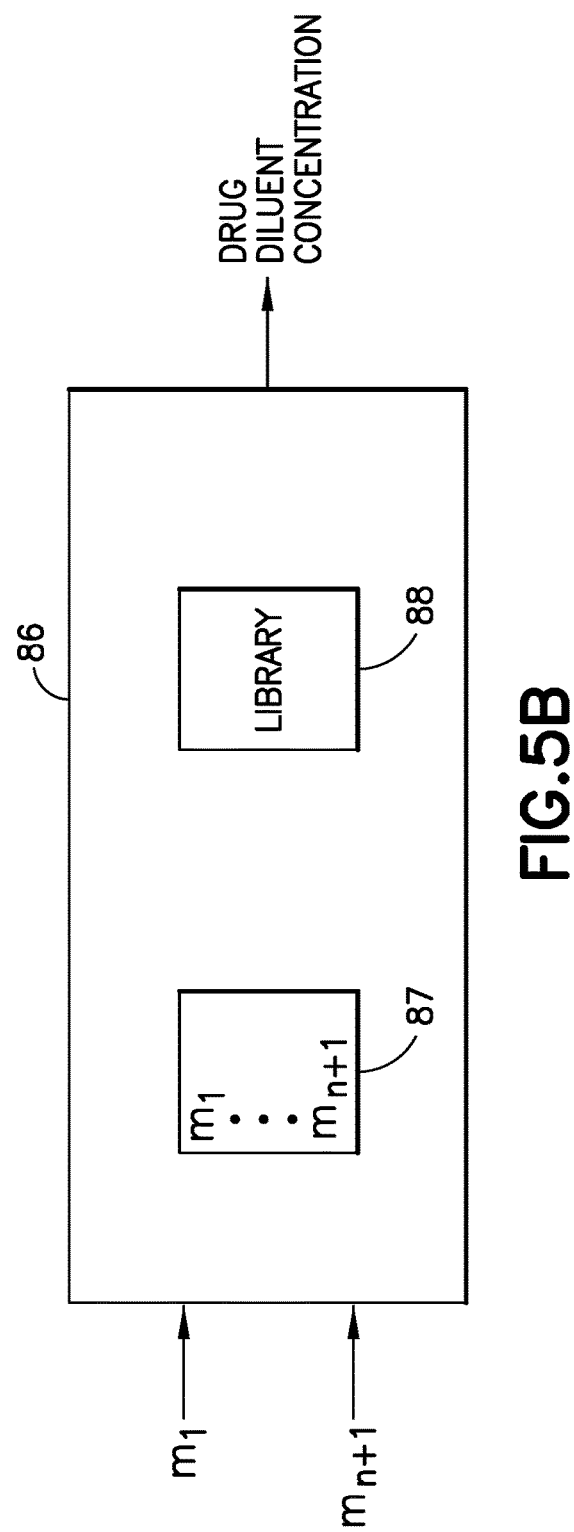
FIG. 5B illustrates an algorithm for classifying the drug in the system of FIG. 5A.

FIG. 5A illustrates an exemplary embodiment where solution properties in a flow cell are monitored in line using flow system (80). In this embodiment, optically clean flow cells or tubes (81) would be assayed by optical techniques for drug characterizations. For example, optically clean flow cells or tubes (81) could be assayed by UV/Visual, Raman Spectroscopy, or Refractive Index in one system to obtain measurements $M_1 \ldots Mn$. If conductivity needs to be measured, electrodes (82) in the flow may be used for conductivity measurements Mn+1. FIG. 5B illustrates a device using an algorithm (86) to compile the solution properties of unknowns ($M_1 \ldots Mn+1$) (87) and compare them to a library of known drugs (88). The flow system (80) could be used at the bedside in a line (83), in an infusion pump (84), or in a waste container system (85).

Bulk chemical properties as determined by analytical techniques are advantageously exploited for drug characterizations. A related application is diagnostic applications related to clinical solutions or diagnostic solutions.

Figure 6:
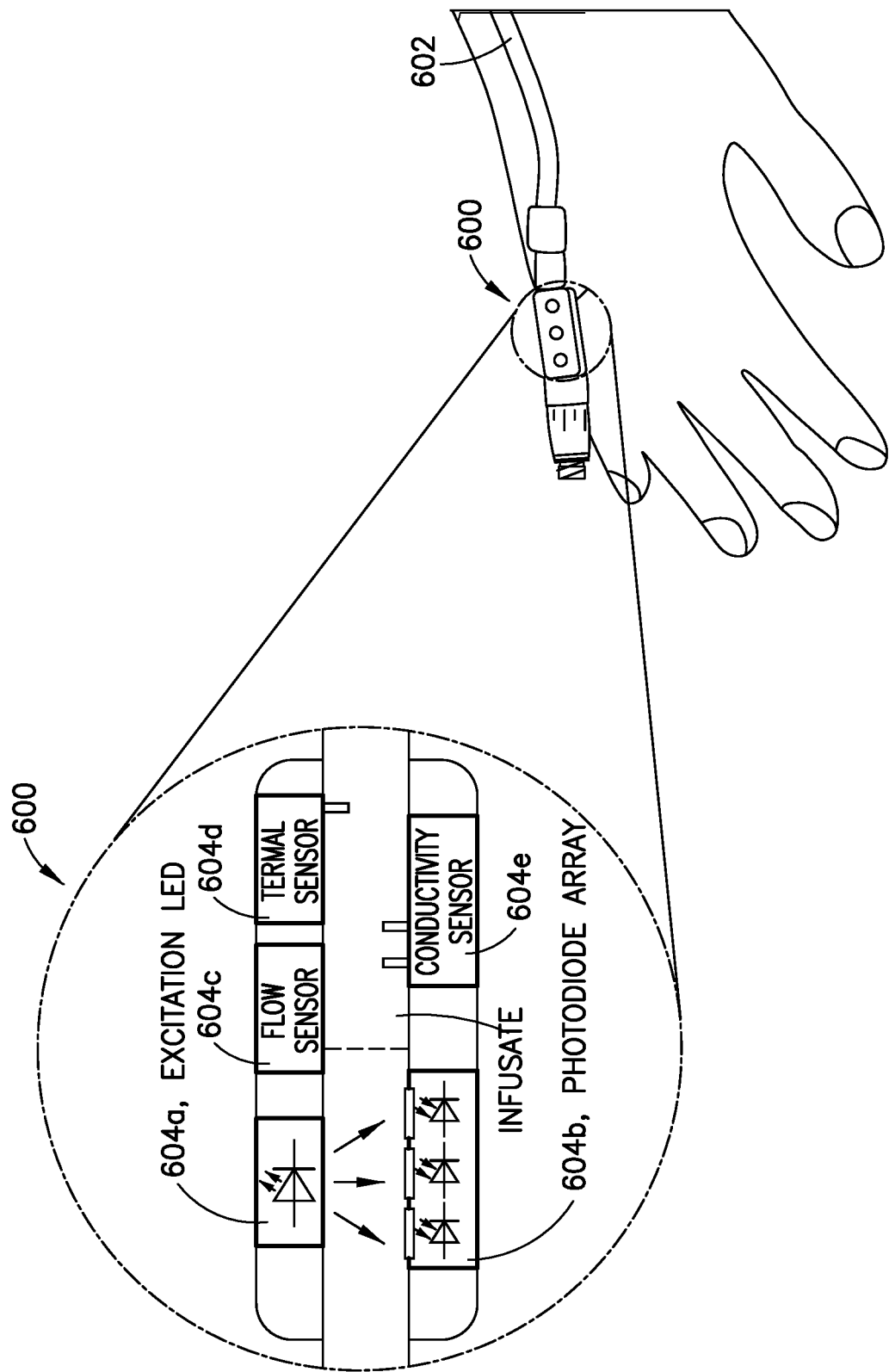
FIG. 6 illustrates an exemplary embodiment of a flow cell comprising multiple sensor types according to the present invention.

An exemplary embodiment of the present invention is illustrated in FIG. 6. A flow cell 600 is preferably incorporated into a catheter 602, or the like, through which fluids to be analyzed flow. The flow cell 600 comprises a plurality of different sensor types 604a-604e. As illustrated, the sensor types include an excitation LED 604a and photodiode array 604b, a flow sensor 604c, a thermal sensor 604d and a conductivity sensor 604e. Utilizing measurements of parameters from two or more of the sensors, the composition or identification of a fluid flowing in the flow cell 600 can be identified with considerably more certainty that in conventional systems that attempt to characterize a substance by a single parameter measurement from a single sensor type.

It should be appreciated that many additions and modifications to the above described embodiments may be made by those of ordinary skill in the art without departing from the scope and spirit of the invention, which is defined by the enumerated claims that follow.

What is claimed is:

1. A method for classifying at least one sample comprising:
   selecting an analytical property measurement technique to apply to the at least one sample;
   applying the analytical property measurement technique to the at least one sample;
   automatically obtaining the results of the analytical property measurement technique applied to the at least one sample;
   automatically determining if the at least one sample can be classified based on the obtained results, wherein only if the at least one sample cannot be classified, automatically selecting and applying another analytical property measurement technique;
   classifying the at least one sample based on the automatically selected analytical property measurement techniques;

wherein the step of selecting an analytical property measurement technique comprises selecting from a group consisting of optical spectroscopy, fluid-mechanic, electrochemical, thermodynamic, and acoustic properties.

2. The method of claim 1, wherein the step of classifying the at least one sample includes classifying multiple samples sequentially.

3. The method of claim 1, wherein the step of classifying the at least one sample includes classifying multiple samples simultaneously.

4. The method of claim 1, wherein the step of classifying the at least one sample includes determining the drug, diluent and concentration.

5. A system for classifying at least one sample comprising:
a housing for containing the at least one sample;
at least one sensing element to measure at least one physical parameter of the at least one sample; and
a processor configured to receive and analyze the at least one physical parameter, and automatically determine if the at least one sample can be classified based on the at least one physical parameter analysis, wherein only if the at least one sample cannot be classified, the processor is configured to automatically select and apply another analytical technique to receive and analyze an additional physical parameter, until the at least one sample is classified.

6. The system of claim 5, further comprising a second sensing element to measure another physical parameter of the sample.

7. The system of claim 5, wherein the housing for containing the at least one sample comprises an optically neutral container.

8. The system of claim 5, wherein the housing for containing the at least one sample comprises an optically clean flow cells or tubes.

* * * * *